United States Patent [19]

Van Doorn et al.

[11] Patent Number: 4,960,747

[45] Date of Patent: Oct. 2, 1990

[54] CATALYST COMPOSITION CONTAINING DIPHOSPHINES HAVING HETEROCYCLIC SUBSTITUENTS

[75] Inventors: Johannes A. Van Doorn; Richard L. Wife; Petrus H. M. Budzelaar, all of Amsterdam, Netherlands

[73] Assignee: Shell Oil Company, Houston, Tex.

[21] Appl. No.: 393,196

[22] Filed: Aug. 14, 1989

Related U.S. Application Data

[62] Division of Ser. No. 233,793, Aug. 19, 1988, Pat. No. 4,880,902.

[30] Foreign Application Priority Data

Aug. 27, 1987 [NL] Netherlands .................. 8702003

[51] Int. Cl.$^5$ .............................................. B01J 31/04
[52] U.S. Cl. .................................... 502/167; 502/162
[58] Field of Search ............................. 502/162, 167

[56] References Cited

U.S. PATENT DOCUMENTS

| | | | |
|---|---|---|---|
| 2,495,286 | 1/1950 | Brubaker | 260/63 |
| 3,689,460 | 9/1972 | Nozaki | 260/63 |
| 3,694,412 | 9/1972 | Nozaki | 260/63 |
| 4,474,978 | 10/1984 | Drent | 560/24 |
| 4,634,793 | 1/1987 | Drent | 560/243 |
| 4,740,625 | 4/1988 | Drent | 568/387 |
| 4,806,630 | 2/1989 | Drent et al. | 528/392 |
| 4,859,764 | 8/1989 | Drent et al. | 502/167 X |

FOREIGN PATENT DOCUMENTS

| | | |
|---|---|---|
| 121965 | 8/1984 | European Pat. Off. . |
| 198696 | 4/1986 | European Pat. Off. . |
| 181014 | 5/1986 | European Pat. Off. . |
| 213671 | 6/1986 | European Pat. Off. . |
| 222454 | 5/1987 | European Pat. Off. . |
| 259914 | 3/1988 | European Pat. Off. . |
| 1081304 | 3/1965 | United Kingdom . |
| 2058074 | 4/1981 | United Kingdom . |

*Primary Examiner*—Patrick P. Garvin
*Attorney, Agent, or Firm*—Dean F. Vance

[57] ABSTRACT

Diphosphines having at least one heterocyclic substituent that includes at least one oxygen, sulphur, or nitrogen atom in a five or six membered ring are useful components in palladium catalyst compositions which have been used to polymerize carbon monoxide and olefinically unsaturated compounds. Remaining substituents, if any, are carbocyclic hydrocarbon groups such as phenyls which are preferably substituted with polar groups in a ring position ortho to the phosphorus. The phosphorus atoms in the diphosphine are connected by a bridging group that contains at least one carbon atom.

9 Claims, No Drawings

CATALYST COMPOSITION CONTAINING DIPHOSPHINES HAVING HETEROCYCLIC SUBSTITUENTS

This is a division of application Ser. No. 233,793, filed Aug. 19, 1988, now U.S. Pat. No. 4,880,902.

FIELD OF THE INVENTION

The invention relates to novel compositions which are suited to be used as catalysts in the preparation of polymers of carbon monoxide with one or more olefinically unsaturated compounds. More specifically, the invention relates to novel diphosphine ligands useful in palladium catalyst compositions.

BACKGROUND OF THE INVENTION

The production of substituted phosphines can be complicated if all of the substituents on the phosphorus atom are not identical. In situations where the production of mixed substituted phosphines is desired, the method of production generally involves the use of an organo alkali metal intermediate, the synthesis of which is often difficult or inefficient.

One class of bidentate phosphorus ligands which are mixed alkyl-aryl diphosphines has become of interest as precursors of catalyst compositions useful in the production of a class of polymeric materials known as polyketones or polyketone polymers. These polyketones are linear alternating polymers of carbon monoxide and at least one ethylenically unsaturated hydrocarbon. Such polymers have repeating units of the formula

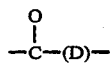

wherein D is a moiety of ethylenically unsaturated hydrocarbon polymerized through the ethylenic unsaturation. Processes for the production of such polymers are illustrated by published European Patent Application Nos. 0,121,965 and 0,181,014 and copending U.S. Pat. No. 4,806,630. The processes usually involve a catalyst composition formed from a compound of a Group VIII metal selected from palladium, nickel or cobalt, the anion of a strong non-hydrohalogenic acid and a bidentate ligand having two Group VA atoms which are preferably phosphorus. Particularly useful as the bidentate phosphorus ligand is the mixed alkyl-aryl diphosphine of the formula

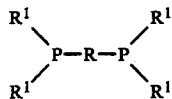

wherein $R^1$ independently is an aryl substituent, and R is a divalent alkylene or substituted alkylene bridging group, often the trimethylene group.

Good results are obtained in the production of polyketones when the phosphine precursor of the catalyst composition is of the above formula wherein each $R^1$ is phenyl and R is trimethylene, the ligand therefore being 1,3-bis(diphenylphosphino)propane. One of the least complicated methods of producing this type of ligand is through the reaction of an alkali metal di($R^1$) phosphide, e.g., sodium diphenylphosphide, and an α,Ω-dihaloalkane such as 1,3-dichloropropane. Corresponding methods produce other bis(diarylphosphino)alkanes.

Recent process developments in polyketone production have shown that particularly good results are obtained on occasion when at least one of the aryl groups has a polar substituent, particularly an alkoxy substituent, in at least one of the ring positions ortho to the phosphorus. Such bidentate phosphorus ligands are represented by the above formula wherein at least one $R^1$ has an alkoxy substituent in a ring position ortho to the phosphorus, e.g., at least one $R^1$ is 2-alkoxyphenyl or 2,6-dialkoxyphenyl.

Monophosphine ligands of the general formula $P(A)_3$ wherein each A is individually an organic substituent tend to make less reactive catalyst compositions than the diphosphine ligands. However, copending U.S. patent application Ser. No. 088,169, now U.S. Pat. No. 4,859,764, establishes that monophosphines having one or more similar or different heterocyclic substituents that contain one or more oxygen, sulphur, or nitrogen atoms in a five or six-membered ring, which ring is bound to the phosphorus atom by one of the carbon atoms in the ring, affords catalyst compositions with attractive activities for the polymerization of carbon monoxide with one or more olefinically unsaturated compounds. Examples of suitable heterocyclic-substituted monophosphines, which may be regarded as being derived from triphenyl phosphine by substitution of one or two of the phenyl groups with a nitrogen-containing heteroaromatic substituent, are: 2-(diphenylphosphino)pyridine, 2-(diphenylphosphino)-1-methylpyrrole, 2-(diphenylphosphino)-1,3,5-triazine and bis(2-pyridyl)phenylphosphine.

SUMMARY OF THE INVENTION

High molecular weight linear polymers of carbon monoxide with one or more olefinically unsaturated compounds (for the sake of brevity referred to as D), in which the monomer units are present in alternating order and which therefore consist of units of the general formula —(CO)—$D^1$—, wherein $D^1$ represents a monomer unit derived from a monomer D used, can be prepared by using catalyst compositions based upon
(a) a palladium compound,
(b) an anion of an acid with a pKa of less than 6, and
(c) a diphosphine of the general formula

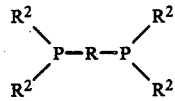

wherein each $R^2$ is independently a similar or different carbocyclic hydrocarbon group which may optionally be substituted with polar groups, or a similar or different heterocyclic substituent having one or more oxygen, sulphur, or nitrogen atoms in a five or six membered ring, which ring is bound to the phosphorus atom by one of the carbon atoms in the ring, at least one $R^2$ being the heterocyclic substituent, and wherein R represents a bivalent bridging group containing at least one carbon atom in the bridge.

It has been found that if one or more of the carbocyclic hydrocarbon groups $R^2$ in the diphosphines are replaced by one or more similar or different heterocyclic substituents, the resulting catalyst compositions have attractive activities for the polymerization of carbon monoxide with one or more olefinically unsaturated compounds.

DESCRIPTION OF THE INVENTION

The present invention includes novel catalyst compositions based upon
(a) a palladium compound,
(b) an anion of an acid with a pKa of less than 6, and
(c) a diphosphine of the general formula

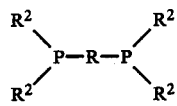

wherein each $R^2$ is independently a similar or different carbocyclic hydrocarbon group which may optionally be substituted with polar groups, or a similar or different heterocyclic substituent having one or more oxygen, sulphur, or nitrogen atoms in a five or six membered ring, which ring is bound to the phosphorus atom by one of the carbon atoms in the ring, at least one $R^2$ being the heterocyclic substituent, and wherein R represents a bivalent bridging group containing at least one carbon atom in the bridge.

The invention further includes the use of these catalyst compositions in the preparation of polymers of carbon monoxide with one or more olefinically unsaturated compounds, as well as to the polymers thus prepared. The invention also includes certain heterocyclic-substituted diphosphines as novel compounds, as well as to a novel process for the preparation of certain heterocyclic-substituted diphosphines.

The palladium compound used in the catalyst compositions as component (a) is preferably a palladium salt of a carboxylic acid and in particular palladium acetate. The preferred component (b) in the catalyst compositions is an anion of an acid with a pKa of less than 4 (determined in aqueous solution at 18° C.) and in particular an anion of an acid with a pKa of less than 2. More specifically, preference is given to an anion of a sulphonic acid, such as para-toluenesulphonic acid or to an anion of a carboxylic acid, such as trifluoroacetic acid. In the catalyst compositions, component (b) is preferably present in a quantity of from 0.5 to 200 and in particular of from 1.0 to 100 equivalents per gram atom of palladium. Component (b) may be taken up in the catalyst compositions in the form of an acid and/or in the form of a salt. Eligible salts include non-noble transition metal salts and in particular copper salts. If desired, components (a) and (b) may be used combined in a single compound. An example of such a compound is the complex Pd(CH₃CN)₂(O₃S—C₆H₄—CH₃)₂ which can be prepared by the reaction in acetonitrile of either palladium chloride with silver para-tosylate, or palladium acetate with para-toluenesulphonic acid.

In the catalyst compositions, component (c) is preferably present in a quantity of 0.1–2 and in particular of 0.75–1.5 mol per mol of palladium compound.

In the diphosphines used as components (c), at least one of the groups $R^2$ should be similar or different heterocyclic substituents having one or more oxygen, sulphur, or nitrogen atoms in a five or six membered ring, which ring is bound to the phosphorus atom by one of the carbon atoms in the ring. Further groups $R^2$ bound to phosphorus in the diphosphines are similar of different carbocyclic hydrocarbon groups which may optionally be substituted with polar groups. Preference is given to diphosphines containing heterocyclic substituents containing only one hetero atom in the ring. In addition of a number of the nitrogen-containing heterocyclic substituents mentioned hereinbefore, the 2-pyridyl group, the 2-furyl group and the 2-thienyl group may also be mentioned. It is preferred to use as components (c) diphosphines in which the heterocyclic substituents are 2-pyridyl or 2-furyl groups.

If similar or different carbocyclic groups are present in the diphosphines used as components (c), one or more of the carbocyclic groups may optionally be substituted with polar groups, these are preferably optionally polar-substituted phenyl groups. As polar substituents that may be present in the carbocyclic hydrocarbon groups may be mentioned, inter alia, dialkyl amino groups, such as dimethyl amino groups, and alkoxy groups, such as methoxy and tertiary butoxy groups. Examples of polar-substituted carbocyclic hydrocarbon groups which may be present in the diphosphines are the 2-methoxyphenyl group and the 2,4-dimethoxyphenyl group.

In the diphosphines used in the catalyst compositions as components (c), R represents a bivalent bridging group containing at least one carbon atom in the bridge. Preferably, bridging group R contains three atoms in the bridge with at least two of which are carbon atoms. Examples of suitable bridging groups R are the —CH₂—CH₂—CH₂— group, the —CH₂—C(CH₃)₂—CH₂— group, the —CH₂—Si(CH₃)₂—CH₂— group and the —CH₂—O—CH₂— group.

Components (c) that are used by preference in the catalyst compositions of the invention are diphosphines wherein each $R^2$ represents a heterocyclic substituent having a structure as defined hereinbefore, or diphosphines that can be represented by the general formula

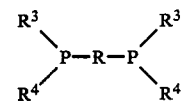

wherein each $R^3$ is a heterocyclic hydrocarbon group as described hereinbefore, and each $R^4$ is a carbocyclic hydrocarbon group which may optionally be substituted with polar groups.

Diphosphines wherein each $R^2$ is a heterocyclic hydrocarbon group were prepared by the reaction in liquid ammonia of an alkali metal M with a monophosphine of the general formula $(R^2)_3P$, followed by the reaction of the alkali metal phosphide $(R^2)_2P$—M obtained thereby with a compound of the general formula X—R—X, in which general formula X represents chlorine or bromine. For example, 2,2-dimethyl-1,3-bis[di(2-furyl)phosphino]propane, was prepared by the reaction of sodium with tri(2-furyl)phosphine, followed by the reaction of the sodium di(2-furyl)phosphide obtained with 1,3-dibromo-2,2-dimethylpropane.

The alkali metal and the substituted triphenylphosphine are contacted in liquid ammonia. Because ammonia normally boils at −33° C., the reaction mixture must be cooled or in the alternative the reaction is conducted under elevated pressure. Although reaction pressures of up to about 4 atmospheres are satisfactory, preferred reaction conditions employ a pressure of substantially one atmosphere and a reaction temperature at which the reaction mixture is maintained in the liquid phase. Such temperatures are typically from about −35° C. to about −100° C. A suitable ratio of alkali metal to phosphine will be from about 1 gram atom of alkali metal to about 3 gram atoms of alkali metal per mol of the phosphine. Best are obtained when about 2 gram atoms of alkali metal are employed per mol of the phosphine. The quantity of liquid ammonia to be used is sufficient to keep the phosphine reactant and the reaction products in solution. Typical amounts of ammonia are from about 1 liter to about 125 liters of ammonia per gram atom of alkali metal, preferably from about 10 liters to about 40 liters of ammonia per gram atom of alkali metal.

The reactants are contacted in a reactor where pressure and/or cooling can be used and where reactant contact can be maintained as by shaking or stirring. No special equipment or materials of construction are required beyond that normally utilized in reactions of very active materials such as alkali metals. Subsequent to reaction an acidic material is often added to consume any unreacted alkali metal and the ammonia is removed as by evaporation. The reaction mixture contains the desired alkali metal phosphide as well as byproducts. The product mixture is separated if desired as by selective extraction but is more conventionally used as such without undue interference by the byproducts. Alternatively, the initial product mixture may be used in a successive reaction without the necessity of removing the ammonia.

Diphosphines of the general formula

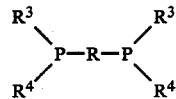

can be prepared for instance by the reaction of a halogen monophosphine of the general formula

with an alkali metal M, followed by the reaction of the alkali metal phosphide obtained with a compound of the general formula X—R—X, in which general formulae X represents chlorine or bromine.

The alkali metal diphenylphosphide wherein one substituent is a carbocyclic hydrocarbon group that is substituted with an alkoxy substituent in at least one ring position ortho to the phosphorus and the other substituent is a heterocyclic hydrocarbon group as defined hereinabove is produced in good yield by the process of the invention. The phosphide product of the present invention is reacted by conventional procedures in liquid ammonia with α,Ω-dihaloalkane to produce a bis[(carbocyclic)(heterocyclic)phosphino]alkane. For example, sodium (2-pyridyl)(phenyl)phosphide is reacted with 1,3-dichloropropane to produce 1,3-bis[(2-pyridyl)(phenyl)phosphino]propane. Such diphosphines are useful as catalyst composition precursors in the production of polyketone polymers.

Thus for instance were prepared the following novel diphosphines:

bis[(2-pyridyl)(phenyl)phosphino]methane,
1,2-bis[(2-pyridyl)(phenyl)phosphino]ethane,
1,3-bis[(2-pyridyl)(phenyl)phosphino]propane,
1,5-bis[(2-pyridyl)(phenyl)phosphino]-3-oxapentane, and
1,8-bis[(2-pyridyl)(phenyl)phosphino]-3,6-dioxaoctane, by the reaction of (2-pyridyl)(phenyl)chlorophosphine with sodium, followed by the reaction of the sodium (2-pyridyl)(phenyl)phosphide obtained thereby with dichloromethane, 1,2-dichloroethane, 1,3-dichloropropane, 1,5-dichloro-3-oxapentane, and 1,8-dichloro-3,6-dioxaoctane, respectively.

In order to enhance the activities of the present catalyst compositions, it is preferred to incorporate a 1,4-quinone as a component (d). In addition to optionally alkyl-substituted 1,4-benzoquinones, there are other eligible 1,4-quinones, such as optionally alkyl-substituted 1,4-naphthoquinones. It is preferred to use 1,4-benzoquinone and 1,4-naphthoquinone as promoters. The quantity of 1,4-quinone used preferably amounts to 10–1000 mol and in particular 25–250 mol per gram atom of palladium.

The polymerization by using the catalyst compositions according to the invention is preferably carried out by contacting the monomers with a solution of the catalyst composition in a diluent in which the polymers are not or virtually not soluble. During the polymerization process the polymers are obtained in the form of a suspension in the diluent. Generally, the polymerization is terminated by cooling and releasing the pressure after the required degree of polymerization is reached. The polymers can be isolated from the suspension, for instance by filtration or centrifugation. Diluents that have been found very suitable are lower alcohols, such as methanol and ethanol.

Eligible olefinically unsaturated compounds that can be polymerized with carbon monoxide by using the catalyst compositions according to the invention are both compounds consisting exclusively of carbon and hydrogen and compounds which, in addition to carbon and hydrogen, contain one or more hetero-atoms. The catalyst compositions according to the invention are preferably used for preparing polymers of carbon monoxide with one or more olefinically unsaturated hydrocarbons. Examples of suitable hydrocarbon monomers are ethene and other α-olefins, such as propene, butene-1, hexene-1 and octene-1, as well as styrene and alkyl-substituted styrenes, such as p-methyl styrene and p-ethyl styrene. The catalyst compositions according to the invention are especially suited to be used for the preparation of copolymers of carbon monoxide and ethene and for the preparation of terpolymers of carbon monoxide with ethene and another olefinically unsaturated hydrocarbon, in particular propene.

The quantity of catalyst composition used in the preparation of the polymers may vary within wide ranges. Per mol of olefinically unsaturated compound to be polymerized, such a quantity of catalyst is preferably used as to contain $10^{-7}$–$10^{-3}$, and in particular $10^{-6}$–$10^{-4}$, gram atom of palladium.

The preparation of the polymers is preferably carried out at a temperature of 20°–200° C. and a pressure of 1–200 bar and in particular at a temperature of 30°–150° C. and a pressure of 20–100 bar. In the mixture to be polymerized, the molar ratio of the olefinically unsaturated compounds relative to carbon monoxide is preferably 10:1–1:5 and in particular 5:1–1:2.

The invention is now illustrated with the aid of the following examples.

EXAMPLE 1

An amount of 2,2-dimethyl-1,3-bis[di(2-furyl)phosphino]propane was prepared as follows. To 500 ml of liquid ammonia present in a stirred reaction vessel which was kept at −78° C. by cooling were consecutively added 41 mmol of sodium and 20 mmol of tri(2-furyl)phosphine. After 4 hours, 18 mmol of ammonium chloride was added to the reaction mixture and, after 15 minutes, 8.7 mmol of 1,3-dibromo-2,2-dimethylpropane. After the addition of 100 ml of tetrahydrofuran, ammonia was removed by evaporation and the residue was refluxed for 2 hours. After the solvent was removed in vacuo, dichloromethane and an aqueous solution of ammonium chloride were added to the residue. The organic layer was separated off, dried and filtered. Finally, the solvent was removed. From analysis of the residue it appeared that the 2,2-dimethyl-1,3-bis[di(2-furyl)phosphino]propane had been obtained in a yield of 70%, calculated on the quantity of 1,3-dibromo-2,2-dimethylpropane employed.

EXAMPLE 2

An amount of bis[(2-pyridyl)(phenyl)phosphino]methane was prepared as follows. To 68 mmol of (2-pyridyl)(phenyl)chlorophosphine dissolved in 120 ml of tetrahydrofuran were consecutively added 140 mmol of sodium and 20 mg of 4,4′-di(t-butyl)-biphenyl. The mixture was refluxed for several days until the colour had changed to dark red and then boiled for another 24 hours. After the reaction mixture was cooled down to −78° C., a solution of 34 mmol of dichloromethane in 25 ml of tetrahydrofuran was added over 30 minutes. After having been kept at −78° C. for another 30 minutes, the reaction mixture was slowly warmed up to room temperature. After the removal in vacuo of the solvent, 75 ml of a diluted sodium hydroxide solution was added to the residue. The mixture was extracted with dichloromethane and the solvent was removed in vacuo. The pure bis[(2-pyridyl)(phenyl)phosphino]methane was isolated from the residue by chromatographic means.

EXAMPLE 3

An amount of 1,2-bis[(2-pyridyl)(phenyl)phosphino]ethane was prepared substantially in the same way as the diphosphine of Example 2, except that, instead of dichloromethane, 1,2-dichloroethane was employed.

EXAMPLE 4

An amount of 1,3-bis[(2-pyridyl)(phenyl)phosphino]propane was prepared substantially in the same way as the diphosphine of Example 2, except that instead of dichloromethane, 1,3-dichloropropane was employed.

EXAMPLE 5

An amount of 1,5-bis[(2-pyridyl)(phenyl)phosphino]-3-oxapentane was prepared substantially in the same way as the diphosphine of Example 2, except that instead of dichloromethane, 1,5-dichloro-3-oxapentane was employed.

EXAMPLE 6

Some 1,8-bis[(2-pyridyl)(phenyl)phosphino]-3,6-dioxaoctane was prepared substantially in the same way as the diphosphine of Example 2, except that instead of dichloromethane, 1,8-dichloro-3,6-dioxaoctane was employed.

EXAMPLE 7

A carbon monoxide/ethene copolymer was prepared as follows. A mechanically stirred autoclave of 300 ml capacity was charged with 250 ml of methanol. After the contents of the autoclave had been brought to a temperature of 83° C., a 1:1 carbon monoxide/ethene mixture was introduced until a pressure of 55 bar was reached. A catalyst solution was then introduced into the autoclave, consisting of:
5.5 ml of methanol,
0.017 mmol of palladium acetate,
0.034 mmol of para-toluenesulphonic acid,
0.024 mmol 2,2-dimethyl-1,3-bis[di(2-furyl)phosphino]propane, and
1.9 mmol of 1,4-benzoquinone.

During polymerization, the pressure was maintained at 55 bar by introducing under pressure a 1:1 carbon monoxide/ethene mixture. After 2.7 hours the polymerization was terminated by cooling the reaction mixture down to room temperature and releasing the pressure. The copolymer was filtered off, washed with methanol and dried at 50° C.

About 13.6 g of copolymer was obtained. The polymerization rate was 2800 g copolymer/g palladium/hour.

EXAMPLE 8

A carbon monoxide/ethene copolymer was prepared substantially in the same way as the copolymer of Example 7, except for the following differences
(a) the polymerization temperature was 82° C. instead of 83° C.,
(b) the catalyst solution used contained
  1,3-bis[(2-pyridyl)(phenyl)phosphino]propane instead of
  2,2-dimethyl-1,3-bis[di(2-furyl)phosphine]propane, and
(c) the polymerization time was 18 hours instead of 2.7 hours.

About 2.0 g of copolymer was obtained. The polymerization rate was 70 g copolymer/g palladium/hour.

EXAMPLE 9

A carbon monoxide/ethene copolymer was prepared substantially in the same way as the copolymer of Example 7, except for the following differences
(a) the polymerization temperature was 82° C. instead of 83° C.,
(b) the catalyst solution used contained
  5.5 ml of methanol,
  0.02 mmol of palladium acetate,
  0.04 mmol of copper para-tosylate,
  0.027 mmol of 1,3-bis[(2-pyridyl)(phenyl)phosphino]propane, and
  6.5 mmol of 1,4-benzoquinone, and
(c) the polymerization time was 3.1 hours instead of 2.7 hours.

About 1.04 g of copolymer was obtained. The polymerization rate was 160 g copolymer/g palladium/hour.

Examples 1–9 are examples according to the invention. Example 1 relates to a novel process for the preparation of a diphosphine of the general formula

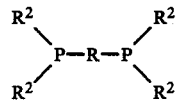

wherein each $R^2$ is the same heterocyclic hydrocarbon group. Examples 2-6 relate to the preparation of novel diphosphines of the general formula

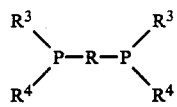

wherein each $R^3$ is the same heterocyclic group and each $R^4$ is the same carbocyclic group. Examples 7-9 relate to the preparation of carbon monoxide/ethene copolymers by using catalyst compositions according to the invention which contain bisphosphines of the preceeding general formula as components (c).

What is claimed is:

1. A catalyst composition useful for polymerizing carbon monoxide and olefinically unsaturated compounds, comprising:
   (a) a palladium compound,
   (b) an anion of an acid with a pKa of less than 6, and
   (c) a diphosphine of the general formula

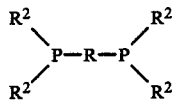

wherein each $R^2$ is independently a similar or different carbocyclic hydrocarbon group, or a similar or different heterocyclic substituent having one or more oxygen, sulphur, or nitrogen atoms in a five or six membered ring selected from 2-pyridyl, 2-furyl or 2-thienyl groups, which substituent is bound to the phosphorus atom by one of the carbon atoms in the ring of the substituent, at least one $R^2$ being the heterocyclic substituent, and wherein R represents a bivalent bridging group containing at least one carbon atom in the bridge.

2. The catalyst composition of claim 1, wherein the palladium compound is a palladium salt of a carboxylic acid.

3. The catalyst composition of claim 1, wherein the acid in component (b) has a pKa less than 2.

4. The catalyst composition of claim 1, wherein each heterocyclic substituent in component (c) contains only one hetero atom in the ring.

5. The catalyst composition of claim 4, wherein the heterocyclic substituent in component (c) is 2-pyridyl or 2-furyl groups.

6. The catalyst composition of claim 5, wherein each $R^2$ is the heterocyclic substituent.

7. The catalyst composition of claim 5, wherein one heterocyclic substituent and one carbocyclic hydrocarbon group are joined to each phosphorus atom in component (c).

8. The catalyst composition of claim 7, wherein each carbocyclic hydrocarbon group in component (c) is substituted with polar groups.

9. The catalyst composition of claim 8, wherein the polar groups are phenyl groups, 2-methoxyphenyl groups, or 2,4-dimethoxyphenyl groups.

* * * * *